United States Patent
Czajkowski et al.

(10) Patent No.: US 7,198,750 B2
(45) Date of Patent: Apr. 3, 2007

(54) SPORE COLLECTION AND ELIMINATION APPARATUS AND METHOD

(75) Inventors: Carl Czajkowski, South Jamesport, NY (US); Barbara Panessa Warren, Port Jefferson, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 803 days.

(21) Appl. No.: 10/396,091

(22) Filed: Mar. 26, 2003

(65) Prior Publication Data

US 2004/0191113 A1 Sep. 30, 2004

(51) Int. Cl.
*A61L 2/08* (2006.01)
*A61L 9/18* (2006.01)

(52) U.S. Cl. ............... 422/22; 422/121; 15/246.3; 96/223; 96/225; 55/DIG. 3; 588/299; 588/305; 588/249.5; 588/900

(58) Field of Classification Search ............ 96/223, 96/224, 225; 55/DIG. 3; 588/299, 301, 588/305, 249.5, 900; 15/246.3; 422/22, 422/121
See application file for complete search history.

(56) References Cited

U.S. PATENT DOCUMENTS 3,907,732 A * 9/1975 Maruyama et al. ........... 524/94
6,656,919 B1 12/2003 Baugh et al. .................. 514/46
6,776,824 B2 * 8/2004 Wen ............................ 96/223

FOREIGN PATENT DOCUMENTS

DE 4141976 A1 * 6/1993
FR 2296292 A * 8/1976

OTHER PUBLICATIONS

Czajkowski, C.J., Evaluation of Static Eliminators Containing Polonium-210, Materials Characterization Journal, vol. 42, No. 1, Jan. 1999, pp. 13-20.
Czajkowski, C.J., "Failure Investigation of 3M Series 900 Static Eliminators," NUREG/CR-5145, Jul. 1988.
Czajkowski, C.J., "Examination of Two 3M Type 902F Static Eliminators," NUREG/CR-5266, Feb. 1989.
Potera, Carol; "Vacuum Device Improves Microbe Collection Methods", American Society of Microbiology, vol. 68, No. 1, Jan. 2002, pp. 5-6.

* cited by examiner

Primary Examiner—E. Leigh McKane
(74) Attorney, Agent, or Firm—Lori-Anne Neiger

(57) ABSTRACT

The present invention is for a spore collection apparatus and its method of use. The portable spore collection apparatus includes a suction source, a nebulizer, an ionization chamber and a filter canister. The suction source collects the spores from a surface. The spores are activated by heating whereby spore dormancy is broken. Moisture is then applied to the spores to begin germination. The spores are then exposed to alpha particles causing extinction.

11 Claims, 1 Drawing Sheet

SPORE COLLECTION AND ELIMINATION APPARATUS AND METHOD

This invention was made with Government support under contract number DE-AC02-98CH10886, awarded by the U.S. Department of Energy. The Government has certain rights in the invention.

BACKGROUND OF THE INVENTION

1. Field of the Invention

The present invention relates to a spore collection apparatus and method, and more particularly to a portable spore elimination apparatus.

2. Description of the Prior Art

Bacterial spores, including anthrax, have been known and used in warfare by a number of countries. Although clean-up efforts are implemented, spores continue to be found over an extended period of time after first exposure. The bacterial endospore is a highly resistant pathogen able to survive for decades without nutrients, moisture or a host. Unlike bacterial cells, bacterial endospores are not easily killed by bleach, alcohol, acids, bases, UV radiation or solvents. Bacterial endospores have an outer exosporial membrane, surrounding outer and inner spore coats and a central core, or protoplast, with DNA and ribosomal material. The difficulty in killing the spores comes from the high resistivity of the spore outer layers to sporocide penetration, and once in host, the spore can survive for a week ortho invivo until growth conditions are optimum for germination and colonization. Therefore liquid sporicides, or gaseous sporicides, require high concentrations of material directly in contact with the spore, for extended periods of time in order to effect a kill rate that reduces the risk to the host organisms. Any spores not killed or removed can remain a threat for many years.

SUMMARY OF THE INVENTION

An object of the present invention is to provide a portable apparatus for the collection and killing of biological spores. Another object of the invention is to provide for a portable apparatus for decontamination of large surfaces, irregular surfaces such as furniture, as well as intricate machinery and moving parts, without impairment of function. Alternatively the apparatus can be adapted to provide spore elimination in building-supplied filtered air systems.

A portable apparatus for the collection and elimination of spores comprising a suction source having a front end collection strip and a back end filter canister for spore collection, a heating element mounted to the suction source back end and being in fluid communication with the front end collection strip, a nebulizer mounted to the heating element for warming and moisturizing the spores and being in fluid communication with the suction source and the heating element, an ionization chamber mounted to the nebulizer for alpha particle irradiation of the spores and a filter canister removeably attached to the ionization chamber wherein the filter canister contains an ionizing material for long term irradiation of the spores.

The ionization chamber contains Polonium 210. The chamber comprises Polonium 210 plates spaced ⅛ inch therewithin apart. The filter canister comprises filters having polonium 210 inserts. The heating element is preheated between 100° F. and 150° F.

A portable apparatus for the collection and elimination of spores comprising a collection element having a collection strip and a suction source wherein the spores are collected from a surface, a heating element connected to the collection element wherein the spores passing are heated to break the dormancy of the spores and activate the spores, a moisture element connected to the heating element wherein moisture is supplied to the spores wherein the spores begin to germinate, a chemical reaction element connected to the moisture element wherein spores are bombarded by an alpha particle source which damages the spore ceasing germination and a containment element connected to the chemical reaction element whereby spores are contained.

A method of collecting and eliminating spores comprising the steps of collecting the spores from a surface, heating spores to activate spores whereby spore dormancy is broken, applying moisture to spores whereby spores begin germination, exposing the spores to alpha particles whereby the spores cease germination and containing the spores wherein the spores are eliminated. Alternately, the spores may be collected from the air, heating the spores to activate spores whereby spore dormancy is broken; applying moisture to the spores whereby spores begin germination; exposing the spores to alpha particles whereby the spores cease germination; and containing the spores wherein the spores are eliminated.

An air filtration system for the collection and elimination of spores comprises intake air ducts where air is collected by a suction source wherein the spores are collected from the air. A heating element connected to the intake air ducts wherein the spores passing are heated to break the dormancy of the spores and activate the spores. A moisture element connected to the heating element wherein moisture is supplied to the spores wherein the spores begin to germinate. A chemical reaction element connected to the moisture element wherein spores are bombarded by an alpha particle source which ceases spore germination. A containment element connected to the chemical reaction element whereby the spores are contained.

DETAILED DESCRIPTION

Figure 1:
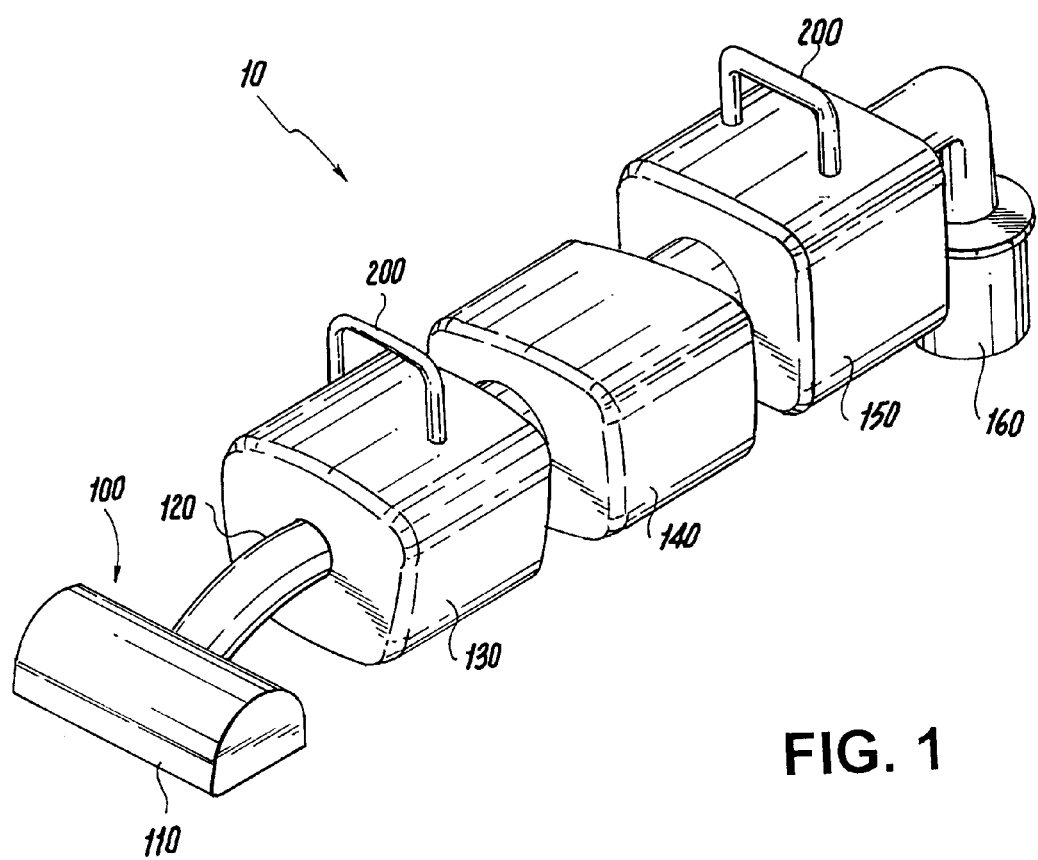
FIG. 1 is a side view of the portable apparatus showing the suction source, heating element, nebulizer, ionization chamber and filter canister.

FIG. 1 shows a portable apparatus 10 for the collection and elimination of spores. The portable apparatus 10 comprises a suction source 100 having a front end collection strip 10 and a back end filter canister 120 for spore collection. The portable apparatus 10 can be placed against a surface where spores are located. The collection strip 110 is in direct contact with the surface. The spores are then collected via a suction force transporting them past the collection strip 110 to the back end 120.

A heating element 130 is mounted to the suction source back end 120. The heating element 130 is in fluid communication with the front end collection strip 110. In the preferred embodiment the heating element is a wire coil wrapped around a ceramic insulator or other such heating systems as known in the art. The heating element will warm the air in the same manner as a common hairdryer. It can be low wattage (less than 1000) since the air needs to be heated to a reasonably low temperature. The heating element 130 is preheated between 100° F. and 150° F. This temperature range is optimal for the activation of the spores. As the collected spores pass through the back end 120 they are exposed to heat whereby spore dormancy is broken.

A nebulizer 140 is mounted to the heating element 130 for warming and moisturizing the spores and being in fluid communication with the suction source 100 and the heating element 130. Following heat shock, the activated spores are exposed to moisture, and the spores then begin the process of germination. The nebulizer 140 may be comprised of a misting device or a steam generator or other devices as known in the art. The nebulizer 140 provides moisture by the addition of water heated to vapor and may then be misted onto spores.

An ionization chamber 150 is mounted to the nebulizer 140 for alpha particle irradiation of the spores. The newly activated spores are exposed to alpha particle bombardment that damages the DNA-containing protoplast causing spore death. The spores are then unable to complete germination and mature into toxin-producing bacterial vegetative cells. In the preferred embodiment, the ionization chamber 150 contains Polonium 210. The Polonium 210 comprises plates spaced ⅛ inch therewithin apart. The use of polonium is the preferred alpha emitter for spore irradiation. Polonium mitigates virtually all of the health and radiation hazards associated with gamma and x-ray sources. Alternatively, other longer-lived alpha emitters can be used if extended storage time, for the device is required.

Alpha particles are charged particles containing two protons and two neutrons that are emitted from the nuclei of certain heavy atoms, such as uranium or polonium when they decay. Because of its size and charge, an alpha particle only travels a few centimeters in air. It can also be stopped or shielded using a sheet of paper. Alpha particles cannot penetrate the dead layer of human skin, but can be very damaging if the source of alpha radiation is inside the body.

Polonium also reduces the amount of shielding required to the external components of the device. The device materials, made of plastic, metal or other materials as known in the art will be sufficient to shield the user from the ionizing radiation, since an alpha particle can be stopped or shielded using a material as thin as a sheet of paper. Thus thin plastics or lightweight materials can be used for construction of the device for the aforementioned reasons. With less shielding the instrument is lighter, thus making it a practical tool for emergency workers or a soldier in the field, where weight can be a factor.

A filter canister 160 is removeably attached to the ionization chamber 150 wherein the filter canister 160 contains an ionizing material for long term irradiation of the spores. In the preferred embodiment the filter canister 160 comprises filters having polonium 210 inserts. High efficiency filters, or HEPA rated filters, are used on vacuum cleaners in industrial and residential applications. These filters are made up of filter media with very tiny openings that are designed to capture the smallest microscopic particles that most traditional filter media or methods are incapable of capturing. The HEPA filtering system with polonium 210 inserts will provide a continuous killing repository for the collected spores.

In the preferred embodiment there may be at least one handle 200 attached to the apparatus 10 for holding and moving the apparatus 10. The at least one handle 200 may be attached to the heating element 130, the nebulizer 140, ionization chamber 150 or filter canister 160. The at least one handle 200 can be placed where the operator can utilize the at least one handle 200 as known in the art. The at least one handle 200 can be made of any hard material such as plastic, metal or other material as known in the art.

A portable apparatus 10 for the collection and elimination of spores comprises a collection element 100 having a collection strip 110 and a suction source wherein the spores are collected from a surface. A heating element 130 is connected to the collection element 100 wherein the spores passing are heated to break the dormancy of the spores and activate the spores.

A moisture element 140 is connected to the heating element 130 wherein moisture is supplied to the spores wherein the spores begin to germinate. A chemical reaction element 150 is connected to the moisture element wherein spores are bombarded by an alpha particle source that damages the spore ceases germination. A containment element 160 is connected to the chemical reaction element whereby spores are contained.

A method of collecting and eliminating spores comprises the first step of collecting the spores from a surface. These spores may be on any surface, large or small, including but not limited to floors, walls, ceilings, window sills, drapery, books, rugs, machinery, paper, glass windows, computers, peripherals and any other surface where spores may be. Heat is applied to the spores causing activation whereby spore dormancy is broken. Moisture is applied to spores whereby spores begin germination. The spores are exposed to alpha particles whereby the spores repair and growth mechanisms are too damaged to complete germination. Cessation of germination and regression cause spore death. The spores are then contained wherein the spores are eliminated.

Alternately, the spores may be collected from the air. The air could be diverted into a duct area for warming/misting and polonium treatment prior to being re-introduced into the building air supply. This alternative embodiment of the apparatus comprises an air filtration system for the collection and elimination of spores comprises intake air ducts where air is collected by a suction source wherein the spores are collected from the air. A heating element is connected to the intake air ducts wherein the spores passing are heated to break the dormancy of the spores and activate the spores. A moisture element is connected to the heating element wherein moisture is supplied to the spores wherein the spores complete activation and begin to germinate. A chemical reaction element is connected to the moisture element wherein spores are bombarded by an alpha particle source which damages the spore and ceases spore growth and maintenance for spore germination. A containment element is connected to the chemical reaction element whereby the spores are contained.

Although the invention is described herein with reference to the preferred embodiment, one skilled in the art will readily appreciate that other embodiments may be substituted for those set forth herein without departing from the spirit and scope of the present invention. As such, the described embodiments are not intended to be exhaustive or to limit the invention to the precise forms disclosed, and obviously many modifications and variations are possible in light of the above teaching. The embodiments were chosen and described in order to best explain the principles of the invention and its practical application. It is intended that the scope of the invention be defined by the claims appended hereto and their equivalents.

The invention claimed is:

1. A portable apparatus for the collection and elimination of spores comprising:
   a. a suction source having a front end collection strip and a back end filter canister for spore collection;
   b. a heating element for heating the spores sufficient to break spore dormancy and activate the spores, said heating element being mounted to the suction source back end and being in fluid communication with the front end collection strip;
c. a nebulizer mounted to the heating element for warming and moisturizing the spores and being in fluid communication with the suction source and the heating element;
d. an ionization chamber mounted to the nebulizer for alpha particle irradiation of the spores; and
e. a filter canister removeably attached to said ionization chamber wherein the filter canister contains an ionizing material for long term irradiation of the spores.

2. A portable apparatus as in claim 1 wherein the ionization chamber contains Polonium 210.

3. A portable apparatus as in claim 2 wherein the Polonium 210 comprises plates spaced 1/8 inch therewithin apart.

4. A portable apparatus as in claim 1 wherein the filter canister comprises filters having polonium 210 inserts.

5. A portable apparatus as in claim 1 wherein the heating element is preheated between 100° F. and 150° F.

6. A portable apparatus as in claim 1 further comprising at least one handle mounted to the portable apparatus.

7. A portable apparatus as in claim 6 wherein the at least one handle is rigidly mounted.

8. A portable apparatus for the collection and elimination of spores comprising:
a. a collection element having a collection strip and a suction source wherein the spores are collected from a surface;
b. a heating element connected to said collection element wherein the spores passing are heated to break the dormancy of the spores and activate the spores;
c. a moisture element connected to said heating element wherein moisture is supplied to the spores wherein the spores begin to germinate;
d. a chemical reaction element connected to said moisture element wherein spores are bombarded by an alpha particle source which damages the spore ceases germination; and
e. a containment element connected to said chemical reaction element whereby spores are contained.

9. A method of collecting and eliminating spores comprising the steps of:
a. collecting the spores from a surface; heating the spores to activate the spores whereby spore dormancy is broken;
b. applying moisture to the spores whereby the spores begin germination;
c. exposing the spores to alpha particles whereby the spores' repair and growth is damaged ceasing germination; and
d. containing the spores wherein the spores are eliminated.

10. A method of collecting and eliminating spores comprising the steps of:
a. collecting the spores from the air;
b. heating the spores to activate the spores whereby spore dormancy is broken;
c. applying moisture to the spores whereby the spores begin germination;
d. exposing the spores to alpha particles whereby the spores are lethally damaged; and
e. containing the spores wherein the spores are eliminated.

11. An air filtration system for the collection and elimination of spores comprising:
a. intake air ducts where air is collected by a suction source wherein the spores are collected from the air;
b. a heating element connected to said intake air ducts wherein the spores passing are heated to break the dormancy of the spores and activate the spores;
c. a moisture element connected to said heating element wherein moisture is supplied to the spores wherein the spores begin to germinate;
d. a chemical reaction element connected to said moisture element wherein spores are bombarded by an alpha particle source which damages the spore and ceases spore growth and maintenance; and
e. a containment element connected to said chemical reaction element whereby spores are contained.

* * * * *